(12) United States Patent
Jianhua

(10) Patent No.: US 10,046,042 B2
(45) Date of Patent: Aug. 14, 2018

(54) MENINGOCOCCAL CONJUGATE VACCINE FOR GROUPS A, C, Y AND W135 AND A PREPARATION METHOD THEREOF

(71) Applicant: BEIJING SANROAD BIOLOGICAL PRODUCTS CO., LTD., Beijing (CN)

(72) Inventor: Wang Jianhua, Beijing (CN)

(73) Assignee: Beijing Sanroad Biological Products Co., Ltd., Beijing (CN)

(*) Notice: Subject to any disclaimer, the term of this patent is extended or adjusted under 35 U.S.C. 154(b) by 0 days.

(21) Appl. No.: 15/197,369

(22) Filed: Jun. 29, 2016

(65) Prior Publication Data

US 2017/0000874 A1  Jan. 5, 2017

(30) Foreign Application Priority Data

Jun. 30, 2015 (CN) .......................... 2015 1 0373194

(51) Int. Cl.
| | | |
|---|---|---|
| *A61K 39/095* | (2006.01) | |
| *A61K 39/00* | (2006.01) | |
| *A61K 39/116* | (2006.01) | |
| *C07K 14/22* | (2006.01) | |

(52) U.S. Cl.
CPC ............ *A61K 39/095* (2013.01); *C07K 14/22* (2013.01); *A61K 2039/55505* (2013.01); *A61K 2039/6087* (2013.01)

(58) Field of Classification Search
CPC ........ A61K 39/095; A61K 2039/55505; A61K 2039/6087; C07K 14/22; C12N 1/20
See application file for complete search history.

(56) References Cited

PUBLICATIONS

Devi et al. Infect. Immun. 65: 1045-1052, 1997.*
Devi et al. FEMS Immunology & Medical Microbiology 14: 211-220, 1996.*
Zollinger et al. Infect. Immun. 65: 1053-1060, 1997.*

* cited by examiner

*Primary Examiner* — S. Devi
(74) *Attorney, Agent, or Firm* — J. Peter Paredes; David G. Rosenbaum; Rosenbaum IP, P.C.

(57) ABSTRACT

The present invention provides a meningococcal conjugate vaccine for groups A, C, Y and W135, which is a tetravalent conjugate vaccine comprising polysaccharide-protein conjugates obtained by respectively conjugating a capsular polysaccharide of Neisseria meningitides groups A, C, Y and W135 to a outer membrane vesicle protein selected from a group consisting of Neisseria meningitides group B serotypes 4 and 15 outer membrane vesicle proteins. The meningococcal conjugate vaccine provided by the present invention may effectively avoid the risk of affecting the immune response to vaccines resulting from immune tolerance and competition between antigenic sites existing in multivalent conjugate vaccines prepared from a single carrier protein; the meningococcal conjugate vaccine provided by the present invention may avoid the safety risk of allergic reactions, toxicity reversion and the like which exist in conjugate vaccines prepared by using TT and DT as carrier proteins; and the meningococcal conjugate vaccine provided by the present invention may enhance immunity to Neisseria meningitides group A and provide a bactericidal antibody having relatively extensive protective effect against Neisseria meningitides group B. Meanwhile, the present invention provides a complete production process of a meningococcal conjugate vaccine for groups A, C, Y and W135, which is applicable to large-scale production. Studies have demonstrated that the present vaccine has good immunogenicity, reliable safety and stable immunity persistence.

7 Claims, No Drawings

MENINGOCOCCAL CONJUGATE VACCINE FOR GROUPS A, C, Y AND W135 AND A PREPARATION METHOD THEREOF

CROSS-REFERENCE TO RELATED APPLICATIONS

The present application claims the benefit of priority to Chinese Patent Application No. 201510373194.4, filed Jun. 30, 2015, and incorporates said Chinese application by reference in its entirety.

TECHNICAL FIELD

The present invention relates to the technical field of immunological technologies, particularly relates to a multivalent meningococcal conjugate vaccine and a preparation method thereof.

BACKGROUND

Epidemic cerebrospinal meningitis (epidemic meningitis) caused by *Neisseria meningitides* (Nm) infection is a worldwide acute respiratory infectious disease, and may be classified into 13 serogroups depending on different capsular polysaccharide compositions of Nm. All serogroups may cause the disease, wherein, Nm diseases are mainly caused by groups A, B, C, Y, and W135, accounting for about 95% of Nm diseases, and they may cause the outbreak and of the epidemic of the diseases.

Vaccination is an economical and effective way to prevent epidemic meningitis diseases. meningococcal conjugate vaccines of different kinds and combinations have developed according to pathogenic characteristics of their epidemic meningitis bacteria, in various countries in the world, including capsular polysaccharide vaccines for group A, group C, groups A and C, and groups A, C, Y and W135, and polysaccharide-protein conjugate vaccines for group A, group C, groups A and C, and groups A, C, Y and W135 having tetanus toxoid (TT), diphtheria toxoid (DT), or non-toxic mutant of diphtheria toxin (CRM197) as a carrier protein. The examples of meningococcal vaccines for group B are VA-MENGOC-BC vaccine produced by Cuban Finlay Institute, which contains B group OMV, C group CPS (capsular polysaccharide) and adjuvant AL (OH)3, and Novartis 4C Men B (Bexsero) vaccine containing fHbp type I protein, Nad A protein and protein NHBA, and New Zealand group B OMV vaccine (MeNZB).

At present, for meningococcal polysaccharide-protein conjugate vaccines that are being developed at home and abroad or already in the market, the carrier protein used is non-toxic mutant of diphtheria toxin (CRM197), tetanus toxoid (TT) or diphtheria toxoid (DT). Although these carrier proteins also may stimulate the organism to produce corresponding antibodies, the antibodies are irrelevant to the prevention of meningococcal diseases and merely have a carrier effect. Moreover, TT and DT are obtained by detoxication of corresponding bacterial toxins with formaldehyde or glutaraldehyde and in the application of Pertussis-Diphtheria-Tetanus triple vaccine, in order to avoid toxicity reversion, it is necessary to add trace formaldehyde or glutaraldehyde to maintain stability of the detoxication effect. However, formaldehyde and glutaraldehyde are not added to conjugate vaccines having TT or DT as a carrier protein, there is thus a risk of the toxicity reversion of the carrier protein. Moreover, tetanus toxoid is a hyperallergenic substance, and it is difficult to completely avoid safety risks including "anaphylaxis" and the like in vaccination of polysaccharide-protein conjugate vaccines having tetanus toxoid (TT) or diphtheria toxoid (DT) as a carrier protein, caused by unthorough detoxication.

In case of vaccination of multivalent polysaccharide conjugate vaccines having a single carrier protein, it is difficult to completely avoid a phenomenon of competition between antigenic sites in the vaccinated organism. As the amount of T cells specific for a same carrier in the vaccinated organism is limited, there is competitive inhibition between various polysaccharide conjugates of the single carrier and thus some antigens may not find corresponding binding sites, thereby decreasing the immunization effect. This phenomenon is called "competition between antigenic sites". It is reported in literatures that TT-induced epitope inhibition is more obvious.

Additionally, only a single carrier protein is used in a multivalent polysaccharide-protein conjugate vaccine, and the kinds of the carrier protein are unitary, leading to a too large vaccination dosage of the carrier protein at each vaccination. Thereby, after repeated vaccination of large amount of carrier proteins, immune tolerance against the carrier protein is formed, affecting immunogenicity of polysaccharides binding to the carrier protein and resulting in decreased immune response. This phenomenon is called "immune tolerance". It has attracted concern and attention of domestic and foreign scholars.

Hence, it is necessary to develop a vaccine that may effectively prevent infectious diseases caused by Neisseria meningitides groups A, C, Y and W135.

SUMMARY OF THE INVENTION

The first object of the present invention is to provide a vaccine that may effectively prevent infectious diseases caused by Neisseria meningitides groups A, C, Y and W135, so as to avoid the safety risk caused by conjugate vaccines having TT and DT as carrier proteins, such as toxicity reversion, allergic reactions and the like, and simultaneously overcome the defect that competition between antigenic sites and immune tolerance caused by multivalent polysaccharide conjugate vaccines may affect the immunization effects. The second object of the present invention is to provide a large-scale production process of a meningococcal conjugate vaccine for groups A, C, Y and W135 having an outer membrane vesicle protein of two different group B serotypes as a carrier protein so as to realize industrialized production.

In order to achieve the first object, the present invention provides a meningococcal conjugate vaccine for groups A, C, Y and W135, which is a tetravalent conjugate vaccine comprising polysaccharide-protein conjugates obtained by respectively conjugating a capsular polysaccharide of Neisseria meningitides groups A, C, Y and W135 to one outer membrane vesicle protein selected from a group consisting of Neissetia meningitides group B serotypes 4 and 15 outer membrane vesicle proteins.

Alternatively, in said vaccine, two capsular polysaccharides selected from a group consisting of Neisseria meningitides groups A, C, Y and W135 capsular polysaccharides are respectively covalently conjugated to a Neisseria meningitides group B serotype 4 outer membrane vesicle protein so as to form two polysaccharide-protein conjugates having the Neisseria meningitides group B serotype 4 outer membrane vesicle protein as a carrier, and the other two capsular polysaccharides are respectively conjugated to a Neisseria meningitides group B serotype 15 outer membrane vesicle protein so as to form the other two polysaccharide-protein conjugates having the Neisseria meningitides group B serotype 15 outer membrane vesicle protein as a carrier.

For example, in an embodiment according to the present invention, capsular polysaccharides of Neisseria meningitides groups A and C, are respectively covalently conjugated to a Neisseria meningitides group B serotype 4 outer membrane vesicle protein to form two polysaccharide-protein conjugates having the Neisseria meningitides group B serotype 4 outer membrane vesicle protein as a carrier, and the other two capsular polysaccharides, i.e. Neisseria meningitides groups Y and W135 capsular polysaccharides are respectively conjugated to a Neisseria meningitides group B serotype 15 outer membrane vesicle protein to form the other two polysaccharide-protein conjugates having the Neisseria meningitides group B serotype 15 outer membrane vesicle protein as a carrier. A total of four polysaccharide-protein conjugates obtained as above are mixed to obtain the tetravalent conjugate vaccine according to the present invention.

In the present invention, the Neisseria meningitides group B includes different subtypes, genotypes and clonal complexes classified according to different typing methods and dominant pathogenic strains from different regions.

In the present invention, strains used for producing the vaccine are obtained from CMCC, but they are not limited to different serotypes of a same serogroup obtained from other sources.

Alternatively, the Neisseria meningitides group A capsular polysaccharide is from strain CMCC29201;

the Neisseria meningitides group C capsular polysaccharide is from strain CMCC29205;

the Neisseria meningitides group Y capsular polysaccharide is from strain CMCC29028;

the Neisseria meningitides group W135 capsular polysaccharide is from strain CMCC29037;

the Neisseria meningitides group B serotype 4 outer membrane vesicle protein is from strain CMCC29356; and the Neisseria meningitides group B serotype 15 outer membrane vesicle protein is from strain CMCC29361.

In the meningococcal conjugate vaccine according to the present invention, the content of free polysaccharides is 15% or less, and the content of free proteins is 3% or less. After an animal is immunized with the vaccine, the sero-conversion rate is 90% or more.

Alternatively, the content of each capsular polysaccharide in the immunizing dose per dose of the meningococcal conjugate vaccine is between 4 μg/ml and 20 μg/ml.

Alternatively, (1) when being in a liquid dosage form, the vaccine optionally comprises an aluminum adjuvant; when the vaccine does not comprise the aluminum adjuvant, a diluents is buffered saline; when the vaccine comprises the aluminum adjuvant, the aluminum adjuvant is aluminum hydroxide, aluminum phosphate or aluminum sulfate; and (2) when being in a lyophilized dosage form, the vaccine optionally comprises an excipient including lactose, sucrose, gelatin, sorbitol, or human serum albumin.

Alternatively, the vaccine is in a lyophilized dosage form, and a diluent for diluting the vaccine is buffered saline, saline; or the diluent is an aluminum adjuvant containing buffer or saline, wherein, the content of aluminum in the diluent is between 0.2 μg/ml and 1.0 μg/ml.

In order to achieve the second object of the present invention, the present invention provides a preparation method of the meningococcal conjugate vaccine according to the present invention, wherein, the preparation of the Neisseria meningitides groups A, C, Y, and W135 capsular polysaccharides comprises the following steps:

(1) Neisseria meningitides groups A, C, Y, and W135 strains are respectively subjected to seed amplification, serial subcultivation to 4th or 5th generation, and then subjected to fermentor culture; the obtained cultures are sterilized with formaldehyde and centrifuged to harvest culture supernatants; cetyl trimethylammonium bromide is added to the culture supernatants to form compound polysaccharides which is collected via centrifugation, the compound polysaccharides are depolymerized by sodium chloride or calcium chloride and step-by-step precipitated with ethanol to obtain crude polysaccharides;

(2) the crude polysaccharides are dissolved in neutral sodium acetate solution; the obtained solution is subjected to cold phenol extraction or ion-exchange and molecular sieve chromatography to obtain refined polysaccharides which are then subjected to filtration sterilization so as to obtain polysaccharide stock solutions meeting standard quality requirements, Alternatively, the preparation of group B serotype outer membrane vesicle proteins comprises the following steps:

(1) Neisseria meningitides group B serotypes 4 and 15 strains are respectively subjected to seed amplification, serial subcultivation to 4th or 5th generation, and then subjected to fermentor culture; the culture is terminated when bacteria grow to late logarithmic growth phase or early stationary phase; and the obtained culture is centrifuged to harvest bacterial mycelia; and (2) dissolution of outer membrane vesicle proteins: the harvested bacterial mycelia are washed with saline or phosphate buffered saline at a pH of 6-6.8 and centrifuged to harvest bacterial mycelia; 0.5-1.5 M NaCl solution or 0.1-0.5 M lithium chloride-sodium acetate extracting solution is added to the resulting bacterial mycelia to dissolve the outer membrane vesicle proteins; the obtained solution is centrifuged to collect a supernatant;

(3) purification of outer membrane vesicle proteins: the supernatant obtained from step (2) is step-by-step precipitated with cold ethanol, and centrifuged to collect precipitate which is reconstituted with water for injection, the obtained solution is step-by-step precipitated by adding ammonium sulfate; the obtained participate is dissolved in water for injection and then depolymerized by adding deoxycholate sodium; a concentrated solution is collected by ultrafiltration of the solution obtained after depolymerization and then precipitated with trichioroacetic acid to obtain precipitate which is collected by centrifugation and dissolved in water for injection; the obtained solution is concentrated by ultrafiltration, and sequentially subjected to ion exchange chromatography, hydrophobic chromatography and molecular sieve chromatography to collect a sample; the sample is sterilized by filtration, and verified by sampling; those meeting quality requirements are qualified outer membrane vesicle protein stock solutions, which are then kept at 2-8° C. or preserved after lyophilization;

(4) specific technical parameters for step (3): cold ethanol is added to the supernatant obtained from step (2) to a final concentration of 55-75%; the obtained precipitate is collected by centrifugation, reconstituted with water for injection; the solution obtained after reconstitution is step-by-step precipitated by adding ammonium sulfate to a final concentration of 15-65%, and precipitate or a supernatant is harvested separately; after the precipitate is reconstituted, deoxycholate sodium is added to the obtained solution to a final concentration of 0.2-1.0%; then the solution is shook and subjected to ultrafiltration to collect a concentrated solution; trichloroacetic acid is added to the concentrated solution to a final concentration of 0.2-3.0% to form precipitate which is collected by centrifugation and dissolved in water for injection; the obtained solution is ultrafiltered and then sequentially subjected to ion exchange chromatography, hydrophobic chromatography and molecular sieve chromatography to collect a sample.

Alternatively, the preparation method comprises a step of mixing the four kinds of polysaccharide-protein conjugate stock solutions to obtain a tetravalent conjugate vaccine, wherein the preparation of polysaccharide-protein conjugate stock solutions comprises the following steps:

Neisseria meningitides capsular polysaccharides are weighted respectively and activated by CNBr to obtain activated carbohydrate chains and then the activated carbohydrate chains are linked to ADH to form capsular polysaccharide-ADH derivatives; after the capsular polysaccharide-ADH derivatives are ultrafiltered to remove free CNBr and ADH, a Neisseria meningitides group B serotype outer membrane vesicle protein is added thereto, mixed well and subjected to condensation reaction with added EDAC to form a covalently conjugated polysaccharide-protein conjugate by means of the bridging function of ADH; the obtained polysaccharide-protein conjugate is ultrafiltered to remove remaining small molecules such as EDAC, concentrated and subjected to molecular sieve chromatography to collect a polysaccharide-protein conjugate with high molecular weight.

The meningococcal conjugate vaccine provided by the present invention may effectively avoid the risk of affecting the immune response to vaccines which results from immune tolerance and competition between antigenic sites existing in multivalent conjugate vaccines prepared from a single carrier protein, and may avoid the safety risk of allergic reactions, toxicity reversion and the like which exist in conjugate vaccines prepared by using TT and DT as carrier proteins, enhance immunity to Neisseria meningitides group A and provide a bactericidal antibody having relatively extensive protective effect against Neisseria meningitides group B. Meanwhile, the present invention provides a complete production process of a meningococcal conjugate vaccine for groups A, C, Y and W135, which is applicable to large-scale production. Studies have demonstrated that the present vaccine has good immunogenicity, reliable safety and stable immunity persistence.

The Present Invention has the Following Advantages:

1. the meningococcal conjugate vaccine for groups A, C, Y and W135 prepared by using two different group B serotypes OMV as a carrier protein shows a good carrier effect and better immune response, and the polysaccharide recovery of conjugates having OMV as a carrier is higher than that of conjugates of various serogroups using TT and DT as a carrier protein, and especially, groups C and W135 have a higher recovery with statistical difference;

2. titer of immunogenic antibody for animal: the antibody titer produced by two immunization injections of conjugates having OMV as a carrier is equal to that produced by three immunization injections of conjugates having TT as a carrier, and higher than that produced by three immunization injections of conjugates having DT as a carrier, which may be related to competition between antigenic sites in multivalent conjugates using a single TT or DT as a carrier protein, and needs to be further studied and analyzed in depth;

3. the antigen compatibility between polysaccharide conjugates of individual serogroups is good, and in a study of effects of immunization injection number in mouse, the anamnestic immune response was significant and serum antibodies showed significant exponential increase, including a increase of antibodies against the two group B serotypes in a serum IgG antibody titer assay after three immunization injections with an interval of 2 weeks;

4. the processes for fermentation culture of strains of individual serogroups and preparation of antigen stock solutions and conjugates are stable and practical, and the product has good quality controllability and stability, which lay a reliable foundation for large-scale production; and 5. it is confirmed by animal safety studies including assays for acute toxicity, abnormal toxicity, allergenicity, pyrogen, sterility, immunogenicity and the like, that the present vaccine has reliable safety and effectiveness.

SPECIFIC MODE FOR CARRYING OUT THE PRESENT INVENTION

The present invention will be described below in detail with reference to detailed embodiments. It needs to be understood that the following examples are merely provided for the purpose of explanation, instead of limiting the scope of the present invention. Without departing from the disciplines and spirits of the present invention, those skilled in the art may make modifications and replacements based on the present invention.

EXAMPLE 1

Example 1 was used to describe the preparation method of the meningococcal conjugate vaccine according to the present invention, The antigen components of individual serogroups in the present invention were as follows:

Neisseria meningitides group A: a strain from Chinese Medical Culture Collection (CMCC) with a registration number of CMCC29201, and the antigen component was a capsular polysaccharide (CPS);

Neisseria meningitides group C: a strain from Chinese Medical Culture Collection (CMCC) with a registration number of CMCC29205, and the antigen component was a capsular polysaccharide(CPS);

Neisseria meningitides group Y: a strain from Chinese Medical Culture Collection (CMCC) with a registration number of CMCC29028, and the antigen component was a capsular polysaccharide (CPS);

Neisseria meningitides group W135: a strain from Chinese Medical Culture Collection (CMCC) with a registration number of CMCC29037, and the antigen component was a capsular polysaccharide (CPS);

Neisseria meningitides group B serotype 4: a strain from Chinese Medical Culture Collection (CMCC) with a registration number of CMCC29356, and the antigen component was an outer membrane vesicle protein (OMV); and Neisseria meningitides group serotype 15: a strain from Chinese Medical Culture Collection (CMCC) with a registration number of CMCC29361, and the antigen component was an outer membrane vesicle protein (OMV).

1. The preparation of groups A, C, Y and W135 capsular polysaccharides:

(1) Neisseria meningitides groups A, C, Y, and W135 strains were respectively subjected to seed amplification, serial subcultivation to 4th or 5th generation, and then subjected to fermentor culture; the obtained cultures were stefflized with formaldehyde and centrifuged to harvest culture supernatants; cetyl trimethylammonium bromide was added to the obtained culture supernatants to form compound polysaccharides which were collected via centrifugation, the obtained compound polysaccharides were depolymerized by sodium chloride and step-by-step precipitated with ethanol to obtain crude polysaccharides;

(2) the crude polysaccharides were dissolved in neutral sodium acetate solution; the obtained solution was subjected to ion-exchange and molecular sieve chromatography to obtain refined polysaccharides which were then subjected to filtration sterilization and verification by sampling; those meeting standard quality requirements were qualified polysaccharide stock solutions, which were kept in a liquid form at a temperature of −20° C. or below.

2. The preparation of Neisseria meningitides group B serotypes 4 and 15 outer membrane vesicle proteins comprise following steps:

(1) Neisseria meningitides group B serotypes 4 and 15 strains were respectively subjected to seed amplification, serial subcultivation to 4th or 5th generation, and then subjected to fermentor culture; the culture was terminated when bacteria grown to late logarithmic growth phase or early stationary phase; and the obtained culture was centrifuged to harvest bacterial mycelia; and (2) dissolution of outer membrane vesicle proteins: the harvested bacteria were washed with saline or phosphate buffered saline at a pH of 6-6.8 and centrifuged to harvest bacterial mycelia; 0.5-1.5 M NaCl solution or 0.1-0.5 M lithium chloride-sodium acetate extracting solution was added to the resulting bacterial mycelia to dissolve the outer membrane vesicle proteins; the obtained solution was centrifuged to collect a supernatant;

(3) purification of outer membrane vesicle proteins: the supernatant obtained from step (2) was step-by-step precipitated with cold ethanol, and centrifuged to collect precipitate which was reconstituted with water for injection; the obtained solution was step-by-step precipitated by adding ammonium sulfate; the obtained participate was dissolved in water for injection and then depolymerized by adding deoxycholate sodium; a concentrated solution was collected by ultrafiltration of the solution obtained after depolymerization and then precipitated with trichloroacetic acid to obtain precipitate which was collected by centrifugation and dissolved in water for injection; the obtained solution was concentrated by ultrafiltration, and sequentially subjected to ion exchange chromatography, hydrophobic chromatography and molecular sieve chromatography to collect a sample; the sample was sterilized by filtration, and verified by sampling; those meeting quality requirements were qualified outer membrane vesicle protein stock solutions, which were then kept at 2-8° C. or preserved after lyophilization;

(4) specific technical parameters for step (3): cold ethanol was added to the supernatant obtained from step (2) to a final concentration of 55-75%; the obtained precipitate was collected by centrifugation, reconstituted with water for injection; the solution obtained after reconstitution was step-by-step precipitated by adding ammonium sulfate to a final concentration of 15-65%, and precipitate or a supernatant was harvested separately; after the precipitate was reconstituted, deoxycholate sodium was added to the obtained solution to a final concentration of 0.2-1.0%; then the solution was shaken and subjected to ultrafiltration to collect a concentrated solution; trichloroacetic acid was added to the concentrated solution to a final concentration of 0.2-3.0% to form precipitate which was collected by centrifugation and dissolved in water for injection; the obtained solution was ultrafiltered and then sequentially subjected to ion exchange chromatography, hydrophobic chromatography and molecular sieve chromatography to collect a sample.

3. The preparation of polysaccharide-protein conjugate stocks:

(1) the preparation of Neisseria meningitides groups A and C conjugates: Neisseria meningitides groups A and C capsular polysaccharides were respectively weighted and activated separately by CNBr to obtain activated carbohydrate chains and then the activated carbohydrate chains were linked to ADH to form capsular polysaccharide-ADH derivatives; after the capsular polysaccharide-ADH derivatives were ultrafiltered to remove free CNBr and ADH, a Neisseria meningitides group B serotype outer membrane vesicle protein was added thereto, mixed well and subjected to condensation reaction with added EDAC to form a covalently conjugated polysaccharide-protein conjugate by means of the bridging function of ADH; the obtained polysaccharide-protein conjugate was ultrafiltered to remove remaining small molecules such as EDAC, concentrated and subjected to molecular sieve chromatography to collect a polysaccharide-protein conjugate with high molecular weight; which was then sterilized by filtration, and verified by sampling; those meeting quality requirements were qualified group A or C polysaccharide-protein conjugate stock solutions, which were kept at 2-8° C.;

(2) the preparation of Neisseria meningitides groups Y and W135 conjugates: Neisseria meningitides groups Y and W135 capsular polysaccharides were respectively weighted and activated separately by CNBr to obtain activated carbohydrate chains and then the activated carbohydrate chains were linked to ADH to form capsular polysaccharide-ADH derivatives; after the capsular polysaccharide-ADH derivatives were ultrafiltered to remove free CNBr and ADH, a Neisseria meningitides group B serotype 15 outer membrane vesicle protein was added thereto, mixed well and subjected to condensation reaction with added EDAC to form a covalently conjugated polysaccharide-protein conjugate by means of the bridging function of ADH; the obtained polysaccharide-protein conjugate was ultrafiltered to remove remaining small molecules such as EDAC, concentrated and subjected to molecular sieve chromatography to collect a polysaccharide-protein conjugate with high molecular weight; which was then sterilized by filtration, and verified by sampling; those meeting quality requirements were qualified group Y or W135 polysaccharide-protein conjugate stock solutions, which were kept at 2-8° C.

4. Dilution, formulation, subpackaging and lyophilization of the meningococcal conjugate vaccine for groups A, C, Y and W135:

(1) according to the measured contents of individual polysaccharides in the polysaccharide-protein conjugate stock solutions for groups A, C, Y and W135, and requirements on dosage for human in each dose, the stock solutions were diluted to a concentration of 8 μg polysaccharide/ml; an additional dose of 12.5% was added to the diluted solutions; 4 polysaccharide-protein conjugates were mixed to obtain a mixed solution as a semi-finished product of the tetravalent conjugate vaccine;

(2) the mixed solution obtained from (1) was diluted by adding a diluent comprising 20 mg/ml lactose as a excipient to the antigen content of the vaccine, mixed well and subpackaged;

(3) the inner package used for the vaccine was a borosilicate vial of 2 ml, 0.5ml per dose; after subpackaging, the vials were partially stoppered by silicon stoppers and placed in a precooled lyophilizer for lyophilization;

(4) lyophilization of the vaccine: subpacked vaccines were placed in the precooled lyophilizer and subjected to freezing, a first sublimation, a second sublimation, drying at a plate temperature (lower than 30° C.), and then stoppered under vacuum, transported out of the lyophilizer, capped with aluminium and kept at 2-8° C.;

(5) the lyophilized vaccines were verified by sampling, and those meeting every quality control requirement were qualified vaccines, which were kept at 2-8° C.

EXAMPLE 2

Example 2 was used to describe the comparison of immunogenicity between meningococcal conjugate vaccines for groups A, C, Y and W135 having different carrier proteins.

1. Object

The immunogenicity of meningococcal conjugate vaccines for groups X C, Y and W135 prepared by using three different carrier proteins (meningococcal group B OMV(ST. 4, 15), TT, and DT) were compared respectively, and a meningococcal polysaccharide vaccine for groups A, C, Y and W135 was used as control. The differences in antibody titer produced by individual vaccines were studied.

2. Experimental Methods 6 weeks old mice were selected. Each group has 20 mice. A vaccine group, a diluent control group and a blank control group were set up separately, and subcutaneously injected in an amount of 0.5 ml per injection at day 0, day 14 and day 21 with a total of 3 injections. The vaccine group was vaccinated with conjugate vaccine comprising groups A, C, Y and W135 polysaccharides in an amount of 1.5 µg for each polysaccharide. Blood was sampled 14 days after each vaccination and serum was separated. The IgG antibody titer in serum from each mouse was measured by using ELISA.

3. Determination of Results

Cutoff value was calculated by using the value A of serum from mice of the diluent control group. If the value of serum from mice of the vaccine group was higher than the Cutoff value, the serum was determined as seroconversion. The seroconversion rate of mice from each group was calculated. Additionally, OD value geometric mean titer (GMT) of each group was calculated based on the OD values of serum from each mouse measured with ELSA.

4. Experimental results were shown in Table 1: Comparison of Immunogenicity Between Meningococcal Conjugate Vaccines for Groups A, C, Y and W135 Having different carrier proteins.

5. Results analysis 5.1 Carrier effect. The results in Table 1 showed the serum titer measured with ELISA in the immune responses for different injection numbers of three carrier protein (B. OMV, TT and DT) conjugate vaccines when a polysaccharide vaccine was used as control. Results indicated that conjugate vaccines had significantly better antibody titer for individual serogoups than the polysaccharide vaccine. The effect of protein carriers in the polysaccharide-protein conjugate vaccines improved the immunogenicity of the polysaccharide vaccine.

5.2 Titer analysis of individual serogroup polysaccharide antibody for different carrier proteins indicated that it could be seen from the comparison of the post-immunization GMT and seroconversion rate for individual serogroup polysaccharides and the effect of injection number that all of the conjugate vaccines meningococcal conjugate vaccines prepared in Example 1) having group B OMVs (serotypes 4 and 15) as a carrier protein had better antibody titer than conjugate vaccines having TT or DT as a carrier protein.

5.3 It was reported in documents that the combined use of multivalent conjugate vaccines using the same carrier protein was likely to lead to a phenomenon of immune tolerance and competitive inhibition between antigenic sites. As a result, the antibody titer and seroconverson rate produced by a meningococcal conjugate vaccine for groups A, C, Y and W135 having two different group B serogroups meningococcal OMVs as earlier proteins are greater than those produced by a conjugate vaccine having a single carrier (TT or DT), which is consistent with results reported by documents,

EXAMPLE 3

Determination of Antibody against Group B for the Meningococcal Conjugate Vaccine for Groups A, C, Y and W135 and Cross-antibody titer against Other Group B serotypes 1. Protocol 1.1 Vaccine for immunization. A meningococcal conjugate vaccine for groups A, C, Y and W135 having OMVs (serotypes 4 and 15) of two group B serogroups as carrier proteins. Batch Nos: 20140601, 20140602 and 20140603.

1.2 Experimental animal. BALB/C mice, each weighted 12-14 g.

1.3 Grouping. Each group had 20 mice with half male mice and half female mice. 5 mice of the same sex were fed in each cage.

TABLE 1

| Carrier Protein | | Injection Number | A | | C | | Y | | W135 | |
|---|---|---|---|---|---|---|---|---|---|---|
| | | | GMT (OD) | Sero-conversion (%) | GMT (OD) | Sero-conversion (%) | GMT (OD) | Sero-conversion (%) | GMT (OD) | Sero-conversion (%) |
| Two Carrier Proteins | B.OMV (ST4.15) | 1 | 0.75 | 80 | 0.81 | 85 | 1.03 | 80 | 0.93 | 85 |
| | | 2 | 2.05 | 100 | 1.85 | 100 | 2.15 | 100 | 2.09 | 100 |
| | | 3 | 2.76 | 100 | 2.53 | 100 | 2.68 | 100 | 2.91 | 100 |
| Single Carrier Protein | TT | 1 | 0.53 | 65 | 0.66 | 60 | 0.73 | 65 | 0.68 | 70 |
| | | 2 | 1.25 | 95 | 1.18 | 90 | 1.35 | 90 | 1.44 | 100 |
| | | 3 | 2.15 | 100 | 1.93 | 100 | 2.03 | 100 | 2.11 | 100 |
| | DT | 1 | 0.52 | 30 | 0.47 | 40 | 0.38 | 25 | 0.45 | 35 |
| | | 2 | 1.16 | 85 | 0.97 | 70 | 1.03 | 80 | 0.85 | 75 |
| | | 3 | 2.03 | 100 | 1.35 | 90 | 1.75 | 95 | 1.66 | 90 |
| Polysaccharide Vaccine | | 1 | 0.13 | 0 | 0.16 | 0 | 0.17 | 0 | 0.20 | 0 |
| | | 2 | 0.53 | 10 | 0.25 | 5 | 0.25 | 0 | 0.36 | 5 |
| | | 3 | 0.66 | 10 | 0.28 | 10 | 0.30 | 10 | 0.29 | 10 |

1.4 Immunization: by subcutaneous injection. Immunizing dose: at every injection, the immunizing dose contained groups A, C, Y and W135 polysaccharides with each polysaccharide being 2.0 µg.

1.5 Immunization procedure. In the whole immunization procedure, there were three immunization injections with an interval of 14 days, that is, immunization were performed via one injection respectively on day 0, day 14 and day 28. Two weeks after the last immunization, blood was sampled and serum was separated. Serum titer of each mouse was measured by ELISA, and geometric mean titer (GMT) of each group was calculated.

2. The serum titer measured by ELISA were shown in Table 2: GMT of serum antibodies against group B and cross-antibodies against group B in mice immunized with the meningococcal conjugate vaccine for groups A, C, Y and W135.

TABLE 2

| Batch No. | Group B Strains GMT | | | | |
|---|---|---|---|---|---|
| | CMCC 29356 (B4) | CMCC 29361 (B15) | B16B6 (2a) | S3446 (14) | CMCC 29316 (2) |
| 20140601 | 6859 | 5577 | 2731 | 2731 | 1859 |
| 20140602 | 7352 | 6309 | 2237 | 3009 | 2133 |
| 20140603 | 6873 | 6309 | 2365 | 2831 | 2237 |

3. Results Analysis

Results shown in Table 2 indicated that in the serum from mice immunized with three batches of the meningococcal conjugate vaccines for groups A, C, Y and W135 respectively, the ELISA titers of antibodies against carrier proteins (serotypes 4 and 15) were every high and the titers of corss-antibodies against other group B strains that have a different serotype (B16B6 (2a), S3446 (14), CMCC29316 (2)) were better, demonstrating that the carrier protein had relatively better immunogenicity and was a wider cross-protective antigen.

EXAMPLE 4

Adjuvant effect of vaccine. Mice were immunized with three dosage forms and adjuvant application forms of meningococcal conjugate vaccines for groups A, C, Y and W135 prepared by using semi-finished products of the same batch, respectively. Blood was sampled from mice. Serum titer of each mouse was measured by ELISA and GMT of each group was calculated. The selection of adjuvant were analyzed and evaluated.

1. Protocol 1.1 Formulation of the vaccine 1.1.1 Antigen sources. Semi-finished vaccine products of the same batchwith the Batch No. 20140604.

1.1.2 The combinations of the three dosage forms with adjuvant were shown in Table 3: Composition of Vaccines in Three Dosage Forms Comprising Different Adjuvants and Antibody Response of Immunization Injections.

TABLE 3

| Semi-finished Vaccine Product Batch No. | Vaccine Dosage form | Adjuvent | Adjuvent Type | Numbers of Injection | Titer Measured by ELISA.GMT | | | | B | |
|---|---|---|---|---|---|---|---|---|---|---|
| | | | | | A | C | Y | W135 | 29356 (B4) | 29361 (B15) |
| 20140604 | Liquid | no | | 1 | 74 | 57 | 64 | 50 | 138 | 97 |
| | | | | 2 | 323 | 224 | 382 | 279 | 760 | 760 |
| | | | | 3 | 667 | 415 | 535 | 529 | 1365 | 1539 |
| | Liquid | Comprised | AL(OH)$_3$ | 1 | 23 | 16 | 27 | 19 | 75 | 68 |
| | | | | 2 | 224 | 214 | 224 | 224 | 535 | 604 |
| | | | | 3 | 3152 | 2881 | 3056 | 2788 | 6857 | 5572 |
| | | | ALPO$_4$ | 1 | 21 | 19 | 28 | 23 | 69 | 80 |
| | | | | 2 | 214 | 224 | 254 | 224 | 521 | 613 |
| | | | | 3 | 3231 | 2788 | 3005 | 2882 | 6873 | 6309 |
| | Lyophilized | Comprised | AL(OH)$_3$ | 1 | 31 | 26 | 31 | 30 | 83 | 83 |
| | | | | 2 | 324 | 268 | 223 | 223 | 633 | 583 |
| | | | | 3 | 3231 | 3152 | 3315 | 3152 | 7831 | 7351 |
| | | | ALPO$_4$ | 1 | 26 | 23 | 28 | 31 | 90 | 83 |
| | | | | 2 | 324 | 287 | 265 | 253 | 583 | 604 |
| | | | | 3 | 3315 | 3005 | 2771 | 3055 | 6873 | 6859 |

1.2 Experimental animal. BALB/C mice with each being 12-14 g.

1.3 Grouping. Each group had 2.0 mice with half male mice and half female mice. 5 mice of the same sex were fed in each cage.

1.4 Immunization of mice: by subcutaneous injection. Immunizing dose: at every injection, the immunizing dose contained groups A, C, Y and W135 polysaccharides with each polysaccharide being 2.0 µg.

1.5 Immunization procedure. In the whole immunization procedure, there were three immunization injections with an interval of 14 days, that is, immunization were performed via one injection respectively on day 0, day 14 and day 28, 14 days after each immunization, blood was sampled and serum was separated. Serum IgG titer of each mouse was measured by ELISA, and geometric mean titer (GMT) in mouse serum from each group was calculated.

2. Experimental results. See Table 3.

3. Results analysis.

3.1 Effect of injection numbers. After three immunization injections of the conjugate vaccines of five combinations listed in Table 3, IgG antibodies against individual serogroups (serotypes) in mouse serum showed significant increase effect with the number of injection increasing, indicating that the anamnestic immune response was relatively good.

3.2 Adjuvant effect. The comparison between two vaccines in a liquid form, one comprising an adjuvant and the other comprising noadjuvant, indicated that:

3.2.1 both of the two vaccines may induce the organism to produce obvious IgG antibody response and anamnestic immune response; and 3.2.2 these two vaccines, one comprising an adjuvant and the other comprising no adjuvant, had significant difference in the rapid production of antibody response under their stimulation, anamnestic immune response after booster immunization and antibody titer.

3.2.2.1 The vaccine comprising no adjuvant may stimulate the organism to produce relatively good antibody response after primary immunization, but after booster immunization, the increase of antibodies was not obvious and the titer of antibodies against individual serogroups (serotypes) was relatively low; and 3.2.2.2 The conjugate vaccine comprising an adjuvant merely stimulated the organism to produce relatively weak antibody response after primary immunization, but after booster immunization, anamnestic immune response was obvious and relatively high antibody titer was produced. In particular, higher antibody titer was produced after the third immunization injection and the effect of injection numbers was more significant.

The experimental results indicated that the addition of aluminum adjuvants to the conjugate vaccine may produce better immune response.

3.3 The comparison of immune response between adjuvant-comprising vaccines in different dosage forms indicated that:

3.3.1 both AL(OH)3 and ALPO4 had relatively good adjuvant effect;

3.3.2 the increase of antibodies against individual groups A, C, Y and W135 and group B (B4 and B15) had no difference; and 3.3.3 the anamnestic immune response effect produced by different numbers of injection were basically the same.

EXAMPLE 5

The present example included an acute toxicity test and an abnormal toxicity test. In the present example, a dose of test article solution was injected into animal subjects (mouse and guinea pigs), and symptoms of toxicity reaction that appeared in the animal subjects and death of the animal subjects were observed in a prescribed time so as to determine whether or not the test articles meets the prescribed quality requirements and determine the safety thereof, using the principle of acute toxicity reaction of different doses of drugs.

1. Experimental Method
1.1 Experimental Animal
1.1.1 Mouse: N1H mice with each being 18-22g; and each group had 5 mice; and
1.1.2 guinea pig: each had a weight of 250-350 g, and each group had 2 guinea pigs.

1.2 Injection Dosage 1.2.1 Abnormal toxicity test. Vaccination dosage prescribed for Abnormal Toxicity Test in Appendix XIIF of Chinese Pharmacopeia (Third part, 2010 Edition):, fasting injection of 0.5 ml for a mouse (the dose for one person); intraperitoneal injection of 5 ml (the dose for 10 persons) for a guinea pig.

1.2.2 Repetitive toxicity test. After administration according to item 1.2.1, it was observed that the animal subjects did not show abnormal symptoms within three days, and remained healthy and normal with an increase of weight when further fed to day 7. At day 8, the subject animals were vaccinated with the same dosage via the same route as those in item 1.2.1 and observed continuously for 7 days. The results were determined.

1.2.3 Acute toxicity test. The concentrated vaccine prepared by using individual polysaccharide-protein conjugate stock solutions for groups A, C, Y, and W135 was administrated with a dose which was 5 times of the dose prescribed for Abnormal Toxicity Test in Appendix KIIF of Chinese Pharmacopeia (Third part, 2010 Edition). Administration dosage: intraperitoneal injection of 0.5 ml (the dose for 5 persons) for a mouse; intraperitoneal injection of 5 ml (the dose for 50 persons) for a guinea pig.

1.2.4 A negative control group was set. 0.5 ml saline was injected intraperitoneally into mice and 5 ml saline was injected intraperitoneally into guinea pigs.

1.3 Determination of Results 1.3.1 Abnormal toxicity test. After vaccination with the test articles, mice and guinea pigs were observed continuously for 7 days. If all of the animals remained healthy and showed no abnormal activities during the observation period and had an increase of weight when the observation period expired, the test articles were determined as qualified test articles.

1.3.2 Repetitive toxicity test. The determination of the experimental results of the first administration was conducted according to the determination standards in item 1.3.1. For determination of the experimental results after the repetitive administration, the weight of the animal subjects was weighted and recorded on day 7, and then the animal subjects were administrated again on day 8 and observed continuously for 7 days; if all of the animals remained healthy and showed no abnormal activities during the observation period and had an increase of weight when the observation period expired, the test articles were determined as qualified test articles.

1.3.3 Acute toxicity test. After vaccination with the test articles, mice and guinea pigs were observed continuously for 7 days. All of the animals remained healthy and showed no abnormal activities during the observation period. When the observation period expired, the animals were weighted. The observation continued until day 14, If all of the animals remained healthy and showed no abnormal activities with an increase of weight, the test articles were determined as qualified test articles.

2. Experimental results were shown in Table 4: Study on Toxicity of Meningococcal Conjugate Vaccine for Groups A, C, W, and Y135.

TABLE 4

| Groups | Animal No. | Weight of Mice(g) | | | Weight of Guinea Pigs (g) | | |
|---|---|---|---|---|---|---|---|
| | | Before | Day 7 | Day 14 | Before | Day 7 | Day 14 |
| Abnormal | 1 | 19.3 | 24.6 | / | 283 | 323 | / |
| Toxicity | 2 | 20.5 | 25.3 | / | 305 | 340 | / |

TABLE 4-continued

| Groups | Animal No. | Weight of Mice(g) Before | Weight of Mice(g) Day 7 | Weight of Mice(g) Day 14 | Weight of Guinea Pigs (g) Before | Weight of Guinea Pigs (g) Day 7 | Weight of Guinea Pigs (g) Day 14 |
|---|---|---|---|---|---|---|---|
| | 3 | 19.5 | 25.1 | / | / | / | / |
| | 4 | 20.0 | 23.9 | / | | | |
| | 5 | 21.3 | 25.3 | / | | | |
| Situations During Observation Period | | Normal food intake and activities; no abnormal situations. | | | Normal food intake and activities; no abnormal situations. | | |
| Repetitive Administration Toxicity | 1 | 18.7 | 23.3 | 29.4 | 315 | 348 | 375 |
| | 2 | 19.5 | 24.5 | 30.3 | 320 | 349 | 386 |
| | 3 | 19.8 | 23.9 | 28.3 | / | / | / |
| | 4 | 20.6 | 24.2 | 28.8 | | | |
| | 5 | 21.0 | 24.5 | 30.3 | | | |
| Situations During Observation Period | | Normal food intake and activities; no abnormal situations. | | After another injection, everything is normal. | Normal food intake and activities; no abnormal situations. | | After another injection, everything is normal. |
| Acute Toxicity | 1 | 19.8 | 21.3 | 26.8 | 320 | 335 | 378 |
| | 2 | 19.5 | 23.1 | 28.3 | 325 | 343 | 388 |
| | 3 | 18.7 | 19.8 | 26.3 | / | / | / |
| | 4 | 19.8 | 21.9 | 26.9 | | | |
| | 5 | 20.5 | 22.4 | 28.0 | | | |
| Situations During Observation Period | | On the day of injection, slightly slow activities and reduced food intake; on the next day, animals recovered gradually, and food intake and activity got improvement obviously. | | Normal food intake and activities; no abnormal situations. | On the day of injection, slightly slow activities and slightly reduced food intake; on the next day, animals recovered gradually, and food intake and activity got improvement obviously. | | Normal food intake and activities; no abnormal situations. |
| Negative Control | 1 | 19.3 | 23.4 | 28.9 | 306 | 342 | 386 |
| | 2 | 20.1 | 24.0 | 30.3 | 311 | 350 | 395 |
| | 3 | 19.6 | 24.1 | 28.9 | / | / | / |
| | 4 | 21.0 | 24.6 | 30.8 | | | |
| | 5 | 19.5 | 25.0 | 31.2 | | | |
| Situations During Observation Period | | Normal food intake and activities; no abnormal situations. | | Normal food intake and activities; no abnormal situations. | Normal food intake and activities; no abnormal situations. | | Normal food intake and activities; no abnormal situations. |

3. Results Analysis

During the observation period for abnormal toxicity of a conventional dose and toxicity of repetitive administration of a conventional dose, animals of each group all showed normal activities and food intake. All of them were healthy and had no abnormal situations and had an increase of weight when the observation period expired.

Merely on the day of injection of a dose which was 5 times of a conventional dose, mice and guinea pigs showed slightly slow activities and reduced food intake; on the next day after vaccination, activity and food intake gradually returned to normal level. During the observation period, no abnormal situations were observed. Till day 7 after the vaccination, all animals had an increase of weight, and till day 14, all animals had a weight approximate to the weight of negative control animals.

The above experimental results indicated that the test articles had reliable safety.

4. Conclusions

In the abnormal toxicity test, the repetitive administration toxicity test and the acute toxicity test, the meningococcal conjugate vaccine for groups A, C, Y and W135 was confirmed as qualified.

EXAMPLE 6

Allergenicity Test

1. The object of the present example was to check whether or not the test article contained allergen substances, to check the severity of an allergic reaction caused by the test article, and to determine the product safety.

2. Experimental principle: when a drug goes into an animal subject as an antigen or a hapten, it would stimulate the organism to produce corresponding antibodies (IgE). When a drug of the same kind is injected into the animal subject, the antigen would hind to the antibodies to form an antigen-antibody complex and stimulate mast cells and basophils to release active mediums, thereby causing localized laryngeal edema, nose-grasping, sneezing, cough, difficult breathing, asphyxia, convulsion, shock and even death, which belong to immediate allergic reaction-anaphylaxis.

3. Protocol

Experimental animals (guinea pigs) were sensitized via 3 consecutive injections of a test article solution with an interval of 1 day, at a dose for one person per injection. Then the sensitized animals were stimulated by timely injecting twice does of the test article. The allergic reactions that appeared in the animals were observed so as to determine whether or not the test article may cause immediate allergic reaction-allergic reaction in animals.

4. Experimental Method 4.1 Grouping: a total of 6 groups were set. Test articles of three batches: meningococcal conjugate vaccines for groups A, C, Y and W135, Batch Nos. 20141001, 20141002, and 20141003. One group was set for each batch.

Positive control group: tetanus toxin.

Negative control group: diluent used for the vaccine and saline.

4.2 Experimental Animals

Healthy, non-pregnant guinea pigs with each being 250-350 g. Each group had 6 guinea pigs.

4.3 Experimental Process

Each group had 6 guinea pigs. guinea pigs were respectively sensitized by intraperitoneally injecting each guinea pig with 0.5 ml of the test article, positive control and negative control with an interval of 1 day for each injection, with a total of 3 injections. Then 6 guinea pigs of the same group were divided into 2 subgroups with each subgroup having 3 guinea pigs. The animals were stimulated via intravenous injection of 1 ml of the test article, the positive control or the negative control corresponding to each group on day 14 and 21 after the day of the first injection, respectively. Each animal was observed for its behaviors and symptoms within 30 minutes after stimulation, so as to see whether the animal has the symptoms of allergic reaction such as nose-grasping, sneezing, difficult breathing, convulsion, shock and even death.

5. Determination of Results

Within 30 minutes after stimulation via intravenous injection of the test article and negative control, the animals shall show no allergic reaction; and if two or more of piloerection, sneezing, retching, 3 consecutive coughs and difficult breathing, or one of convulsion (spasm), shock and death appeared, the test article would be determined as unqualified.

Animals of the positive control group showed allergic reaction, and none of animals of the negative control group showed allergic reaction. The experiments were determined as valid.

6. Experimental results were shown in Table 5: Allergenicity Test for Meningococcal Conjugate Vaccine for Groups A, C, Y and W135.

TABLE 5

| Group | | Animal No. | Numbers of Injection Number | | | First stimulation (Day 14) | Second stimulation (Day 21) | Results |
|---|---|---|---|---|---|---|---|---|
| | | | 1 | 2 | 3 | | | |
| Test Article (Vaccine) | 20140501 | 1 | √ | √ | √ | Guinea pigs were normal without abnormal responses during the observation period. | | No allergy symptoms; Qualified |
| | | 2 | √ | √ | √ | | | |
| | | 3 | √ | √ | √ | | | |
| | | 4 | √ | √ | √ | | Guinea pigs were normal without abnormal responses during the observation period. | No allergy symptoms; Qualified |
| | | 5 | √ | √ | √ | | | |
| | | 6 | √ | √ | √ | | | |
| | 20140502 | 1 | √ | √ | √ | Guinea pigs were normal without abnormal responses during the observation period. | | No allergy symptoms; Qualified |
| | | 2 | √ | √ | √ | | | |
| | | 3 | √ | √ | √ | | | |
| | | 4 | √ | √ | √ | | Guinea pigs were normal without abnormal responses during the observation period. | No allergy symptoms; Qualified |
| | | 5 | √ | √ | √ | | | |
| | | 6 | √ | √ | √ | | | |

| Group | | Animal No. | Numbers of Sensitization Injection | | | First stimulation (Day 14) | Second stimulation (Day 21) | Results |
|---|---|---|---|---|---|---|---|---|
| | | | 1 | 2 | 3 | | | |
| Test Article (Vaccine) | 20140503 | 1 | √ | √ | √ | Guinea pigs were normal without abnormal responses during the observation period. | | No allergy symptoms; Qualified |
| | | 2 | √ | √ | √ | | | |
| | | 3 | √ | √ | √ | | | |
| | | 4 | √ | √ | √ | | Guinea pigs were normal without abnormal responses during the observation period. | No allergy symptoms; Qualified |
| | | 5 | √ | √ | √ | | | |
| | | 6 | √ | √ | √ | | | |
| Negative Control | Diluent Used for Vaccine | 1 | √ | √ | √ | Guinea pigs were normal without abnormal responses during the observation period. | | No allergy symptoms; Negative control was tenable. |
| | | 2 | √ | √ | √ | | | |
| | | 3 | √ | √ | √ | | | |
| | | 4 | √ | √ | √ | | Guinea pigs were normal without abnormal responses during the observation period. | No allergy symptoms; Negative control was tenable. |
| | | 5 | √ | √ | √ | | | |
| | | 6 | √ | √ | √ | | | |
| Negative Control | Saline for Injection | 1 | √ | √ | √ | Guinea pigs were normal without abnormal responses during the observation period. | | No allergy symptoms; Negative control was tenable. |
| | | 2 | √ | √ | √ | | | |
| | | 3 | √ | √ | √ | | | |
| | | 4 | √ | √ | √ | | Guinea pigs were normal | No allergy |

TABLE 5-continued

| | | | | | | | | |
|---|---|---|---|---|---|---|---|---|
| | | 5 | √ | √ | √ | | without abnormal responses during the observation period. | symptoms; Negative control was tenable. |
| | | 6 | √ | √ | √ | | | |
| Positive Control | Tetanus | 1 | √ | √ | √ | Difficult breathing, convulsion, death | | Three guinea pigs had the symptom of anaphylactic shock, and died; the positive control was tenable. |
| | | 2 | √ | √ | √ | Difficult breathing, convulsion, death | | |
| | | 3 | √ | √ | √ | Difficult breathing, convulsion, death | | |
| | | 4 | √ | √ | √ | | Difficult breathing, convulsion, death | Three guinea pigs had the symptom of anaphylactic shock, and died; the positive control was tenable. |
| | | 5 | √ | √ | √ | | Difficult breathing, convulsion, death | |
| | | 6 | √ | √ | √ | | Difficult breathing, convulsion, death | |

7. Results Analysis 7.1 Negative control and positive control experiments were tenable respectively, indicating that the experimental results are valid.

7.2 For the three batches of meningococcal conjugate vaccine for groups A, C, Y and W135, after the first stimulation and the second stimulation, none of the sensitized experimental animals showed symptoms of allergic reaction. All these three vaccines were qualified in allergy test.

8. Conclusions

Meningococcal conjugate vaccine for groups A, C, Y and W135 with batch Nos. 20141001, 20141002 and 20141003 were qualified in the allergenicity test.

EXAMPLE 7

Pyrogen Test in Rabbit

1. Experimental Object: the present experiment was focused on determining whether or not the amount of pyrogen contained in the test article met the quality requirements by intravenously injecting a certain dose of the test article into rabbits and observing the increase of rabbit body temperate within a prescribed time.

2. Experimental method and determination standard: Appendix XIID of Chinese Pharmacopoeia (Part 3, 2010 Edition).

3. Experimental results were shown in Table 6: Pyrogen Test in Rabbit for Meningococcal Conjugate Vaccine for Groups A, C, Y and W135.

TABLE 6

| Vaccine Batch No. | Rabbit No. | | | | Determination of Results |
|---|---|---|---|---|---|
| | Increase of Rabbit Body Temperature | | | | |
| | 1 | 2 | 3 | Sum | |
| 20141001 | 0 | 0.2 | 0.3 | 0.5 | Qualified |
| 20141002 | 0.4 | 0.1 | 0.1 | 0.6 | Qualified |
| 20141003 | 0.2 | 0.1 | 0.2 | 0.5 | Qualified |

4. Results Analysis

For the three batches of vaccines, the sums of body temperature increase in three rabbits for each batch of vaccine were 0.5° C., 0.6° C. and 0.5° C., respectively. The experimental results were stable. The three batches of vaccines met the quality requirements.

5. Conclusions

The three batches of vaccines were qualified in the pyrogen test in rabbits.

EXAMPLE 8

Sterility Test

1. Object: The sterility test aimed to determine the sterility of a test article by checking whether or not microorganisms grew in a sensitive medium comprising the test article.

2. Experimental conditions and methods: see Appendix XIIA of Chinese Pharmacopoeia (Part 3, 2010 Edition).

3. Experimental results were shown in Table 7: Sterility Test for Meningococcal Conjugate Vaccine for Groups A, C, Y and W135.

TABLE 7

| | | Medium | | | | | | Results |
|---|---|---|---|---|---|---|---|---|
| | | Thioglycollate Medium | | Martin Broth, Modified | | Nutrient Broth | | |
| | | Culture Temperature | | | | | | |
| Test Article | | 20-25 | 30-35 | 20-25 | 30-35 | 20-25 | 30-35 | |
| Vaccine | 20141001 | − | − | − | − | − | − | No microorganic growth |
| | 20141002 | − | − | − | − | − | − | No microorganic growth |
| | 20141003 | − | − | − | − | − | − | No microorganic growth |
| Negative Control | | −− | − | − | − | − | − | No microorganic growth |
| Positive Control | | + | + | + | + | + | + | microorganic growth |

4. Results Analysis

There was microorganic growth for the positive control; and there was no microorganic growth for the negative control. The experimental results were valid. For the three batches of vaccines, there was no microorganism growth. The results of the sterility test met the quality standard requirements.

5. Conclusion

The three batches of vaccines were qualified in the sterility test.

EXAMPLE 9

Immunogenicity Test

1. Object

The antigen component of a vaccine is an exogenous substance from a pathogenic organism. When the antigen goes into an organism via vaccination, the immune system of the organism will make response to the antigen, including specific antibodies produced by humoral immune response, synergistic effect of cellular immune response and immune support system, thereby achieving a function of preventing diseases.

Besides normal immune system and synergetic immune functions of the systems in an organism, the nature and function of the antigen as an exogenous substance that activates the immune function in the organism is critical. The immunogenicity test is a quantitative detection means used for detecting the intensity of specific antibodies produced after the antigen goes into the organism and activates the humoral immune response.

2. Experimental Method 2.1 Experimental animals and grouping. 6 weeks old NTH mice with each being 12-14 g were selected. Each group had 20 mice with half male mice and half female mice. 5 mice of the same sex were fed in one cage.

2.2 Group setting.

2.2.1 The following groups were set respectively: blank control group: no solution was injected and animals were fed under the same condition;

2.2.2 diluent control group: 0.85% saline comprising 0.6 mg/ml AL(OH)3 adjuvant;

2.2.3 test article group: meningococcal conjugate vaccine for groups A, C, Y and W135, batch Nos: 20141001, 20141002 and 20141003.

2.3 Animal Immunization 2.3.1 immunization dose: the dose was based on individual serogoup (A, C, Y and W135) pspolysaccharides conjugated to the carrier protein, each dose (0.5 ml) comprised 2 μg pspolysaccharides for each serogroup pspolysaccharide.

2.3.2 Immunization route: abdominal hypodermic injection for mice.

2.3.3 Immunization procedure: animals were vaccinated with one dose respectively on day 0, 14 and 21.

2.4 Sampling, Separation and Determination of Serum 7 days after the last immunization (on day 28), blood was collected through the retro-orbital plexus of mice, and the serum was separated. The serum IgG antibody titer was determined by indirect ELISA.

3. Determination standard.

Cutoff value was given by using the value A of serum from mice of the diluent control group. If the value of serum from mice of the test article group was higher than the Cutoff value, the serum was determined as seroconversion. If more than 90% of the mice in the vaccine test article group had a serum antibody titer greater than the Cutoff value, the test articles were determined as qualified.

4. Experimental results were shown in Table 8: Immunogenicity Test for Meningococcal Conjugate Vaccine for Groups A, C, Y and W135.

TABLE 8

| | Serogroup (type) | | | | | | | | | | | |
| --- | --- | --- | --- | --- | --- | --- | --- | --- | --- | --- | --- | --- |
| | Measurement (GMT) | | | | | | Seroconversion rate | | | | | |
| | Measurement | | | | | | | | | | | |
| Batch No. | A | C | Y | W135 | B4 | B15 | A | C | Y | W135 | B4 | B15 |
| 20141001 | 2.39 | 2.15 | 2.45 | 2.55 | 2.83 | 2.45 | 100 | 100 | 100 | 100 | 100 | 100 |
| 20141002 | 2.52 | 2.31 | 2.22 | 2.63 | 2.63 | 2.39 | 100 | 100 | 100 | 100 | 100 | 100 |
| 20141003 | 2.33 | 2.29 | 2.19 | 2.29 | 2.60 | 2.50 | 100 | 100 | 100 | 100 | 100 | 100 |

Note:
the Cutoff value of diluents serum was 0.268.

5. Analysis and Determination of Results

When the titer was measured by ELISA, the Cutoff value of diluent serum was 0.268. For test article groups of the three batches of vaccine (each group 20 mice), the serum GMT measurement for antibody against individual serogroups (types) antigens were between 2.22-2.63, which was greater than the Cutoff value and determined as seroconverson with a seroconversion rate of 100%.

6. Conclusion

In the immunogenicity test for test article groups of three batches of vaccine, the seroconversion rate for individual serogroups (serotypes) achieved 100%, meeting the quality standard requirements. The test articles were qualified.

Although the present invention is described in detail with reference to the general descriptions and detailed embodiments above, it is obvious to those skilled in the art to make changes or modifications based on the present invention. Hence, the changes or modifications which are made without departing from the spirits of the present invention fall into the protection scope claimed by the present invention.

What is claimed is:

1. A tetravalent meningococcal capsular polysaccharide conjugate vaccine comprising isolated capsular polysaccharide of each of groups A, C, Y and W135 *Neisseria meningitidis*, wherein the capsular polysaccharide of each of the *Neisseria meningitidis* groups is conjugated to an isolated outer membrane vesicle protein selected from the group consisting of group B *Neisseria meningitidis* serotype 4 outer membrane vesicle protein and group B *Neisseria meningitidis* serotype 15 outer membrane vesicle protein.

2. The tetravalent meningococcal capsular polysaccharide conjugate vaccine of claim 1, wherein the capsular polysaccharides of first two *Neisseria meningitidis* groups selected from the group consisting of A, C, Y and W135 are conjugated to the group B *Neisseria meningitidis* serotype 4 outer membrane vesicle protein and the capsular polysaccharides of the other two *Neisseria meningitidis* groups other than the first two and selected from the group consisting of A, C, Y and W135 are conjugated to the group B *Neisseria meningitidis* serotype 15 outer membrane vesicle protein.

3. The tetravalent meningococcal capsular polysaccharide conjugate vaccine of claim 1 or 2, wherein the group B *Neisseria meningitidis* serotype 4 outer membrane vesicle protein and the group B *Neisseria meningitidis* serotype 15 outer membrane vesicle protein are of different subtypes, genotypes and clonal complexes classified according to different typing methods and of pathogenic *Neisseria meningitidis* group B strains from different regions.

4. The tetravalent meningococcal capsular polysaccharide conjugate vaccine of claim 3, wherein
   the *Neisseria meningitidis* group A capsular polysaccharide is of strain CMCC29201;
   the *Neisseria meningitidis* group C capsular polysaccharide is of strain CMCC29205;
   the *Neisseria meningitidis* group Y capsular polysaccharide is of strain CMCC29028;
   the *Neisseria meningitidis* group W135 capsular polysaccharide is of strain CMCC29037;
   the group B *Neisseria meningitidis* outer membrane vesicle protein is of strain CMCC29356 and
   the group B *Neisseria meningitidis* outer membrane vesicle protein is of strain CMCC29361.

5. The tetravalent meningococcal capsular polysaccharide conjugate vaccine of claim 4, wherein the content of each of the capsular polysaccharides in an immunizing dose of the conjugate vaccine is between 4 microgram per ml and 20 microgram per ml.

6. The tetravalent meningococcal capsular polysaccharide conjugate vaccine of any one of claims 1-5, wherein
   (a) when being in a liquid dosage form, the conjugate vaccine optionally comprises an aluminum adjuvant; when the vaccine does not comprise the aluminum adjuvant, the conjugate vaccine comprises a diluent for diluting the conjugate vaccine; when the conjugate vaccine comprises the aluminum adjuvant, the aluminum adjuvant is aluminum hydroxide, aluminum phosphate or aluminum sulfate and
   (b) when being in a lyophilized dosage form, the conjugate vaccine optionally comprises an excipient selected from the group consisting of lactose, sucrose, gelatin, sorbitol and human serum albumin.

7. The tetravalent meningococcal capsular polysaccharide conjugate vaccine according to claim 6, wherein the conjugate vaccine is in a lyophilized dosage form and is diluted with saline, buffered saline, or a buffer or saline diluent containing an aluminum adjuvant, wherein the content of the aluminum in the diluent is between 0.2 milligram per ml and 1.0 milligram per ml.

* * * * *